United States Patent [19]
Cline et al.

[11] Patent Number: 5,526,814
[45] Date of Patent: Jun. 18, 1996

[54] AUTOMATICALLY POSITIONED FOCUSSED ENERGY SYSTEM GUIDED BY MEDICAL IMAGING

[75] Inventors: Harvey E. Cline, Schenectady; Ronald D. Watkins, Niskayuna, both of N.Y.

[73] Assignee: General Electric Company, Schenectady, N.Y.

[21] Appl. No.: 443,229

[22] Filed: May 17, 1995

Related U.S. Application Data

[63] Continuation of Ser. No. 149,484, Nov. 9, 1993, abandoned.
[51] Int. Cl.$^6$ .................................................. A61B 5/055
[52] U.S. Cl. ................... 128/653.2; 601/3; 607/97
[58] Field of Search ................... 128/653.1, 653.2, 128/653.5, 660.03; 607/97; 601/2–4

[56] References Cited

U.S. PATENT DOCUMENTS

| | | | |
|---|---|---|---|
| 4,896,673 | 1/1990 | Rose et al. | 128/660.03 |
| 4,914,608 | 4/1990 | Lebihan | 364/557 |
| 4,924,198 | 5/1990 | Laskaris | 335/216 |
| 5,036,836 | 8/1991 | Terai et al. | 601/4 |
| 5,178,135 | 1/1993 | Uchiyama et al. | 601/4 |
| 5,187,658 | 2/1993 | Cline et al. | 364/413.13 |
| 5,213,102 | 5/1993 | Kudo et al. | 128/660.03 |
| 5,247,935 | 9/1993 | Cline et al. | 128/653.2 |
| 5,305,749 | 4/1994 | Li et al. | 128/653.2 |

OTHER PUBLICATIONS

"Effects of Physical Parameters on High Temperature Ultrasound Hyperthermia", Ultrasound in Med. & Biol., vol. 16, No. 4, pp. 409–420, 1990.

*Primary Examiner*—Ruth S. Smith
*Attorney, Agent, or Firm*—Lawrence P. Zale; Marvin Snyder

[57] ABSTRACT

An automatically positioned focussed energy transducer system facilitates medical procedures by allowing a physician to interactively view the position the focal point of a focussed energy transducer superimposed upon a medical image and computer generated model of internal structures of a patient. A tracking device tracks the position and orientation of the ultrasound transducer. A medical imaging system creates an image of internal structures of the patient near the location of the energy transducer. A general purpose computer either receives a model of internal structures constructed in advance, or employs a medical imaging device to create the model. The general purpose computer displays selected surfaces of the model in an orientation and view which coincides with the medical image acquired. A superposition device receives the position and orientation of the ultrasound transducer from the tracking device and superimposes a symbol on the images corresponding to the position of the energy transducer relative to the patient. The physician then selects an internal structure to be destroyed which the general purpose computer determines the locations which the focal point must scan in order to destroy the structure. An actuator, coupled to the general purpose computer causes the focal point of the energy transducer to scan these locations which the physician adjusts the intensity of energy provided to the focal point by an input device.

7 Claims, 3 Drawing Sheets

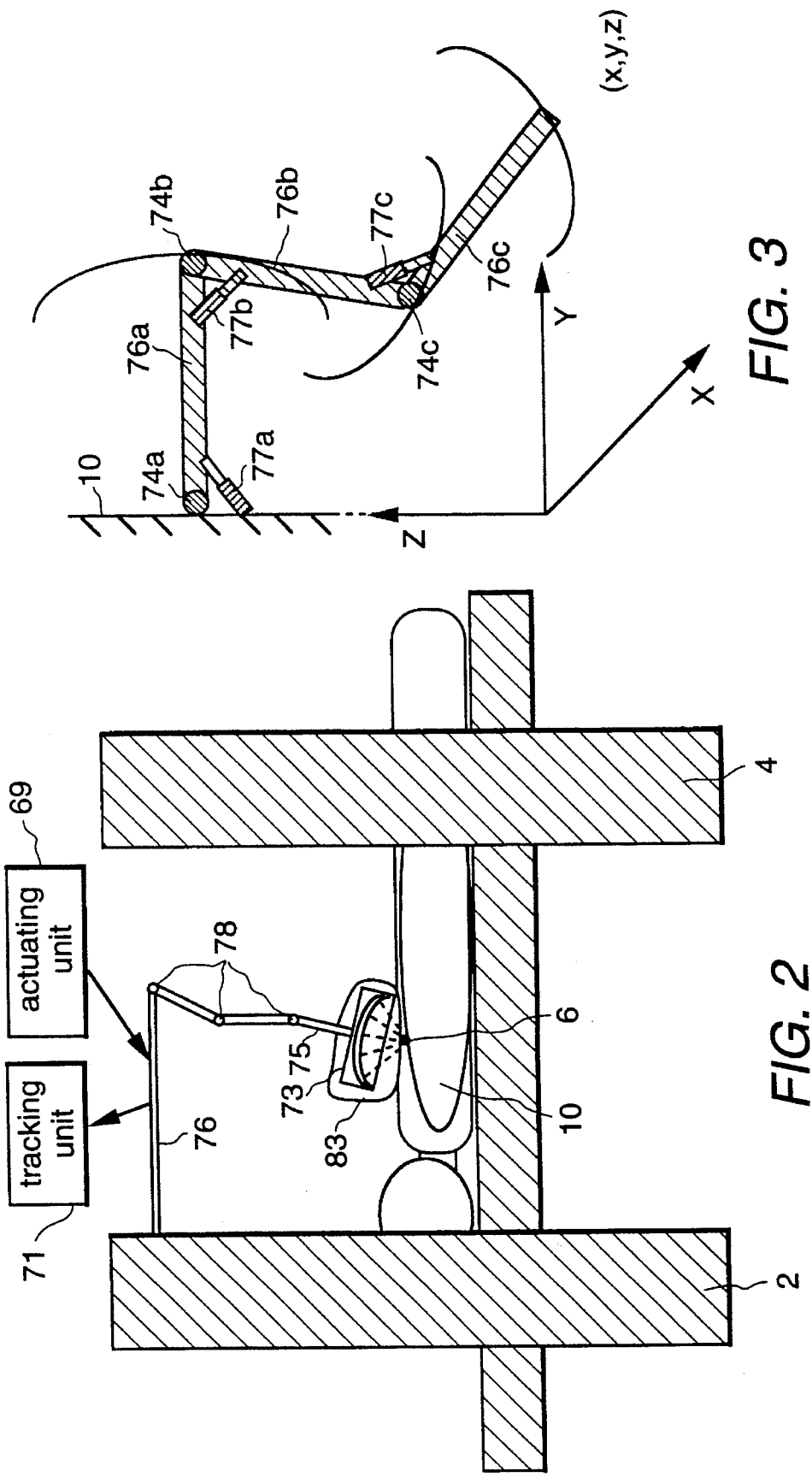

AUTOMATICALLY POSITIONED FOCUSSED ENERGY SYSTEM GUIDED BY MEDICAL IMAGING

CROSS REFERENCE TO RELATED APPLICATIONS

This application is a Continuation of application Ser. No. 08/149,484, filed Nov. 9, 1993 now abandoned.

This application is related to U.S. patent applications "Magnetic Resonance Guided Focussed Ultrasound Surgery" by Harvey Cline et al. Ser. No. 07/854,040 filed Mar. 19, 1992; "Magnetic Resonance Surgery Using Heat Waves Produced with Focussed Ultrasound" by Harvey Cline et al. Ser. No. 07/751,259 filed Aug. 29, 1991; "Magnetic Resonance Surgery Using Heat Waves Produced with a Laser Fiber" by Harvey E. Cline et al. Ser. No. 08/125,520, filed Sep. 24, 1993, U.S. Pat. No. 4,924,198 "Superconductive Magnetic Resonance Magnet without Cryogens" by Evangelos T. Laskaris issued May 8, 1990; "Open Gradient Coils for Magnetic Resonance Imaging" by William Barber et al. Ser. No. 08/146,346 filed Nov. 2, 1993; "MR Imaging System For Minimally Invasive Surgery" by Roemer et al. Ser. No. 08/146,345 filed Nov. 2, 1993; and "Manually Positioned Focussed Energy System Guided by Medical Imaging" by Harvey Cline, Ronald Watkins Ser. No. 08/149,485 filed Nov. 9, 1993, all assigned to the present assignee and hereby incorporated by reference.

BACKGROUND OF THE INVENTION

1. Field of the Invention

The present invention relates to a system for enabling medical procedures to be performed by ultrasonic heating and more particularly to a system for enabling selective heating of tissue guided by medical imaging.

2. Description of Related Art

Conventional medical imaging provides the radiologist with internal views of a patient's anatomy. Magnetic resonance (MR) imaging provides excellent contrast between different tissues and is useful in planning surgical procedures. A tumor in a patient is much more visible in an MR image than as seen in actual surgery because the tumor and normal tissue often look similar in surgery. The tumor can also be obscured by blood during surgery.

Tumors have been selectively destroyed in cancer patients using focussed ultrasound heating at the University of Arizona, as reported by B. E. Billard, K. Hynynen and Robert. B. Roemer "Effects of Physical Parameters on High Temperature Ultrasound Hyperthermia" Ultrasound in Med. & Biol. Vol. 16, No. 4, pp. 409–420, 1990 and hereby incorporated by reference. The patient is first scanned in an MRI system to locate the tumor and plan a safe trajectory between the entry and target points. A view of the heated region is provided with the use of MR temperature sensitive pulse sequences. Known MR temperature sensitive pulse sequences are described in U.S. Pat. No. 4,914,608 "In-vivo Method for Determining and Imaging Temperature of an Object/Subject from Diffusion Coefficients Obtained by Nuclear Magnetic Resonance" by Denis LeBihan, Jose Delannoy, and Ronald L. Levin issued Apr. 3, 1990. Experiments on animals show that a heated zone above a critical temperature destroys tissue. This zone increases in size with time as the heat is applied to reach a steady state or both temperature and heat flow. If the maximum temperature is limited to 100 deg. C., then the heated zone, the area exceeding a critical temperature causing destruction of tissue, approaches 1 centimeter in diameter. It is difficult to predict the heated zone geometry because the heat flow depends on the profusion of blood as well as the tissue thermal properties.

However, it is difficult to determine the location of the energy focal point without activating the energy transducer.

Currently there is a need for a method of selectively destroying tissue non-invasively without affecting adjacent healthy tissue.

OBJECTS OF THE INVENTION

It is an object of the present invention to allow automated positioning of a focussed ultrasound device guided by a medical imaging device to accurately destroy selected tissue.

It is another object of the present invention to allow a physician to selectively destroy internal tissues of a patient with a small amount of invasiveness.

SUMMARY OF THE INVENTION

An automatically positioned focussed energy system enables a physician to selectively heat a region of a patient. A medical imaging system acquires three-dimensional data of internal structures of said patient to create a computer generated model of these internal structures which is provided to a general purpose computer capable of manipulating and selectively displaying portions of the model.

A tracking means determines the position and orientation of the focal point of an energy transducer.

The general purpose computer initiates images to be acquired at a selected orientation and position which preferably encompasses the focal point. The images are displayed on a display device along with internal structures of the model in a corresponding view. These may be temperature sensitive images.

A superposition device receives the position and orientation of the energy transducer and superimposes a symbol indicating the position and orientation of the energy transducer on the image of the display device.

The physician employs a pointing device to interactively select an internal structure of the model to be destroyed causing the general purpose computer to determine locations within said patient which correspond to the internal structure.

An actuating device coupled to the general purpose computer receives the locations determined by the general purpose computer and scans the focal point of the energy transducer through these locations. The physician may interactively adjust the intensity of the energy provided to the focal point as the focal point is scanned.

BRIEF DESCRIPTION OF THE DRAWINGS

The features of the invention believed to be novel are set forth with particularity in the appended claims. The invention itself, however, both as to organization and method of operation, together with further objects, may best be understood by reference to the following description taken in conjunction with the accompanying drawing in which:

FIG. 2 is an enlarged view of the focussed energy transducer, tracking unit, and and partial MR imaging system of FIG. 1.

FIG. 3 is an enlarged view of the focussed energy transducer of FIGS. 1 and 2 as it would be used on the patient.

DETAILED DESCRIPTION OF THE INVENTION

Figure 1:
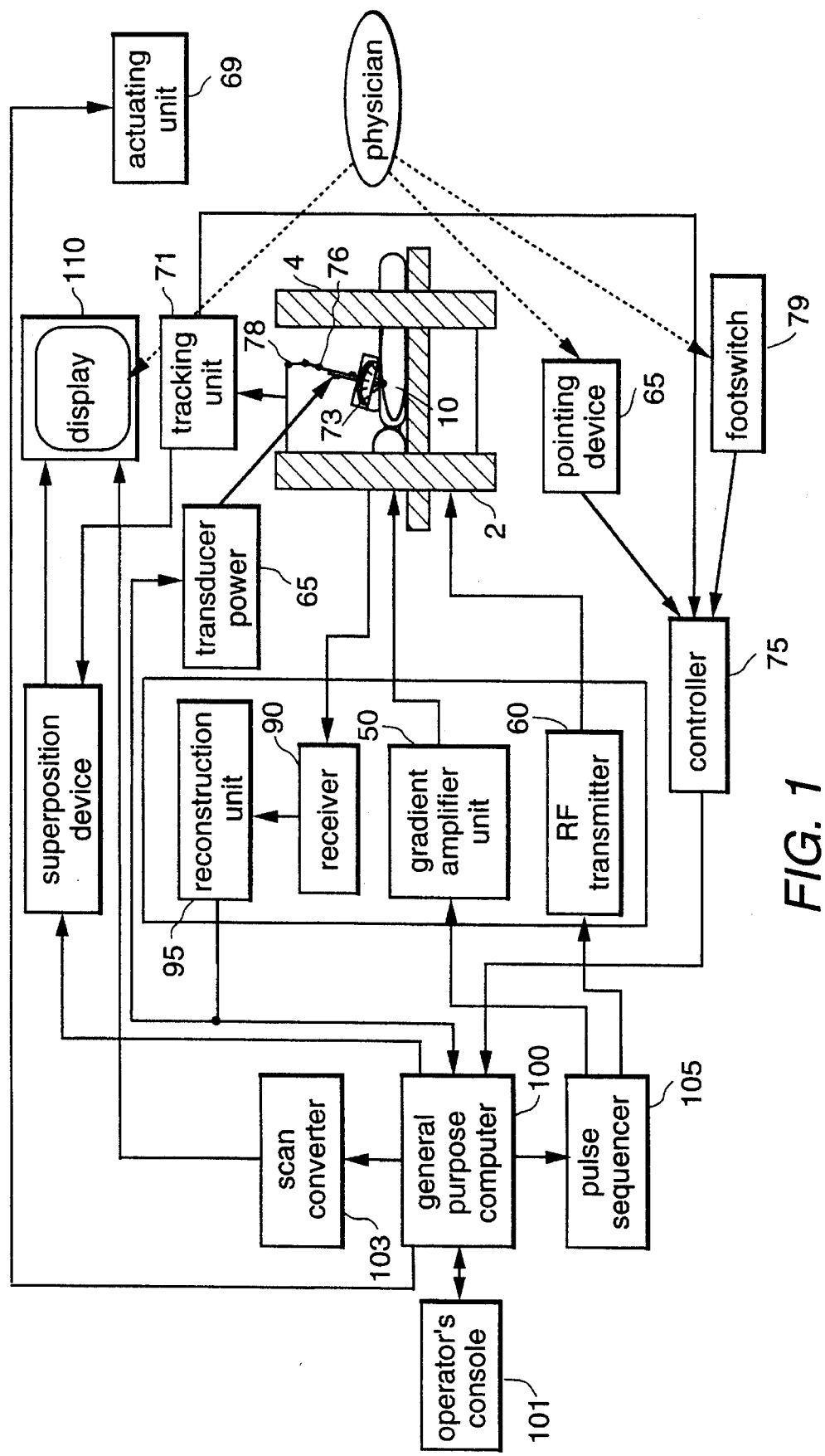
FIG. 1 is a block diagram of an embodiment of a magnetic resonance (MR) imaging system according to the present invention.

A block diagram of the manually positioned focussed energy system guided by medical imaging of the present invention is shown in FIG. 1. In the preferred embodiment, a magnetic resonance (MR) imaging system is employed for medical imaging. A patient 10 is positioned within an open main magnet of the MR imaging system, having two superconducting rings 2, 4 which provides a static, spatially homogeneous magnetic field over an imaging volume between the rings. A gradient amplifier 50 provides power to a plurality of gradient coil sets located within rings 2, 4, each producing a magnetic field gradient in a specified direction. An RF transmitter 60, supplies the necessary power to RF coils to nutate nuclear spins within a patient in the imaging volume. The gradient coil sets within rings 2, 4 produce magnetic field gradients over the imaging volume without restricting access to the imaging volume, or the patient within the imaging volume.

A general purpose computer 100 either receives a model simulating internal structures of patient 10, or constructs one with the medical imaging system.

Once the model is acquired or constructed, it may be displayed on a display device 110 at any desired angle or orientation. The display parameters may be provided to general purpose computer 100 through an operator's console 101. Many different methods of selectively imaging the model or surfaces of the model are disclosed in U.S. Pat. No. 5,187,658 issued Feb. 16, 1993 "System and Method for Segmenting Internal Structures Contained Within the Interior Region of a Solid Object" by H. E. Cline, W. E. Lorensen; "System for Displaying Solid Cuts For Surfaces of Solid Models" by W. E. Lorensen, H. E. Cline, B. Teeter, S. Ludke; "Solid Model Generation by Span Method Using Dividing Cubes" by H. E. Cline, W. E. Lorensen; "Apparatus And Method for Displaying Surgical Cuts In Three-Dimensional Models" by H. E. Cline, W. E. Lorensen, S. Ludke; and "System for 3D Scan Conversion of a Polygonal Model Into A Point and Normal Format, Displayed Utilizing an Accelerator Circuit" by H. E. Cline, W. E. Lorensen, all assigned to the present assignee and hereby incorporated by reference.

Once the physician has viewed the region which a medical procedure is to be performed, he may then position a focal point of an energy transducer 73 capable of concentrating energy at the focal point, at an approximate position within patient 10. Energy transducer 73 is connected to a mechanical arm 76 which is fixed with respect to patient 10. Sensors on joints 78 of mechanical arm 76 indicate the position and orientation of energy transducer 73 attached to the end of the arm. A tracking unit 71 determines the position and orientation of energy transducer 73 from the sensors on joints 78. Knowing the focal length of ultrasound transducer 73, the tracking unit 71 may also calculate the position of the focal point. In the preferred embodiment, a set of infrared cameras act as a tracking unit 71 (this was manufactured by the PIXSYS corporation) and track the positions of two light emitting diodes (LEDs) attached to the hand-held energy transducer 73. Controller 75 receives the location and orientation of energy transducer 73 from tracking unit 71 and provides this information to general purpose computer 100.

A superposition device 94, coupled to tracking unit 71, general purpose computer 100 and display device 110, receives the position and orientation of energy transducer 73, and the field of view and image plane information from general purpose computer 100 and superimposes a symbol representing the location and position of energy transducer 73, or its focal point, on an image of the model on display device 110 to aid the physician in interactively positioning the energy transducer before energizing the energy transducer. The arm may also be equipped with locking mechanisms, to stabilize the energy transducer in a desired position.

The physician then may trigger an image to be acquired with a device such as a footswitch 79 through the controller 75 which activates a pulse sequencer 105. Pulse sequencer 105 controls the timing and activation of gradient amplifier 50 and RF transmitter 60 to produce magnetic field gradients and RF radiation which cause an MR response signal to be emitted by tissue of patient 10 near energy transducer 73.

A receiver 90 receives the emitted MR response signal from the patient 10, and provides this signal to a reconstruction unit 95. Reconstruction unit 95 produces data for an MR image of patient 10. The image data is provided to general purpose computer 100. General purpose computer then employs the locations and orientation of the model, and the MR image and assimilates them into a superimposed image as viewed from a single location which is displayed on operator's console 101. General purpose computer 100 also provides the signal to a scan converter 103 which changes the format of the signal and provides it to a display device 110 visible to the physician. This allows accurate positioning without the consequence of heating or destroying healthy tissue.

The physician, may interactively alter the superimposed images on display device 110 by rotating and displaying selected surfaces of the model. The physician then indicates tissue desired to be destroyed by selecting an internal structure of the model, or tracing out the tissue desired to be destroyed. The physician may select the tissue with a pointing device 67 through controller 75 and general purpose computer 100, or by other computer input means.

Once the tissues to be destroyed is defined, general purpose computer 100 directs actuating unit to activate mechanical arm 76 and cause the focal point of energy transducer 73 to scan the entire volume of the tissue desired to be destroyed. The model defines the extent and shape of the selected volume.

The intensity, pulse rate, pulse width and period between pulses for the energy transducer may be either preset or provided interactively during a medical procedure to operator's console 101. The physician interactively adjusts the intensity provided to the focal point as the focal point is scans through the volume of the selected tissue. The physician may initiate MR temperature sensitive images to be acquired to monitor the tissue being heated indicating if the focal point is located in the proper tissue. The physician may also initiate non-temperature sensitive images to be acquired which indicates a different morphology of destroyed tissue. These images may be used for the physician to interactively adjust the intensity of the energy transducer, or turn it off. The image choices may be provided by the physician by footswitch 79 or pointing device 67. Footswitch 79 or other input device near the physician may also be used to control the scanner timing and provide rudimentary controls such as changing scan modes or scan type. This may be used to toggle between spin echo imaging, gradient echo imaging or any other menu of preset parameters.

Power for energy transducer 73 is provided by a transducer power unit 65 which is controlled by general purpose computer 100.

Display device 110 should be visible to the physician. Due to the large magnetic fields employed by MR imaging, a display device near the physician would have to be a liquid crystal display. Also since there is substantial RF radiation, it should be enclosed in a suitable RF shielding to minimize RF interference.

The present invention may obtain images at planes through the focal point or planes bisecting an axis through the focal point and energy transducer 73 to determine intervening tissues.

An enlarged view of the focussed energy transducer 73, tracking unit 71, and patient positioned within the bore of the open magnet of the MR imaging system is shown in FIG. 2. A tissues desired to be destroyed 6, such as a tumor or cyst, lies within patient 10. A physician (not shown for clarity) holds energy transducer 73 by handle 68 and positions energy transducer 73 such that the focal point is approximately on tissue 6. Energy transducer 73 is immersed energy conducting medium. In the case of energy transducer 73 being a focussed ultrasound transducer, the energy conducting medium may be water. A patient interface 83 being a membrane filled with the energy conducting medium surrounds energy transducer 73 and is placed in contact with patient 10 such that a path from energy transducer 73 to patient 10 is almost entirely energy conducting medium, except for the intervening membranes containing the conducting medium. Due to the flexible nature of patient interface 83, the physician may move energy transducer 73 to position the focal point in different locations while maintaining a path almost entirely composed of conducting medium between the energy transducer and patient 10.

Mechanical arm 76 may be a conventional arm capable of at least 3 degrees of motion, being able to move its end to any location (x,y,z) within the imaging volume. In the preferred embodiment, 4 degrees of freedom were employed. The fifth degree of freedom was not necessary since the beam of the energy transducer was radially symmetric. Since the mechanical arm will be within the magnets of the MR imaging system, it would have to be made of materials which are compatible with MR imaging. The magnetic susceptibility should be similar to that of the patient being imaged. Therefore it should be constructed with pistons actuators or screw actuators. One such embodiment is shown in FIG. 3 mechanical arm 76 has three links 74a, 74b, 74c connected in series with a joints connecting links. Joint 74a is located between link 76a and a fixation point (here it may be magnet ring 2) and allows the end of link 76a to swing in the Z direction with some motion in the Y direction. Link 76a is actuated by a hydraulic actuator 77a connected between link 76a and the fixation point. Similarly, joint 74b connects link 76a to link 76b and allows the end of link 76b to move in the X direction with some motion in the Z direction relative to joint 74b. Actuator 77b causes this motion. Joint 74c connects link 76b to link 76c and allows the end of link 76c to move in the Y direction with some motion in the Z direction relative to joint 74c. Actuator 77c causes this motion. Actuating unit 69, is able to translate a desired end position (x,y,z) into the required signals to actuators 77a, 77b, 77c to cause the end of mechanical arm 76 to be positioned at the desired location.

Figure 4:
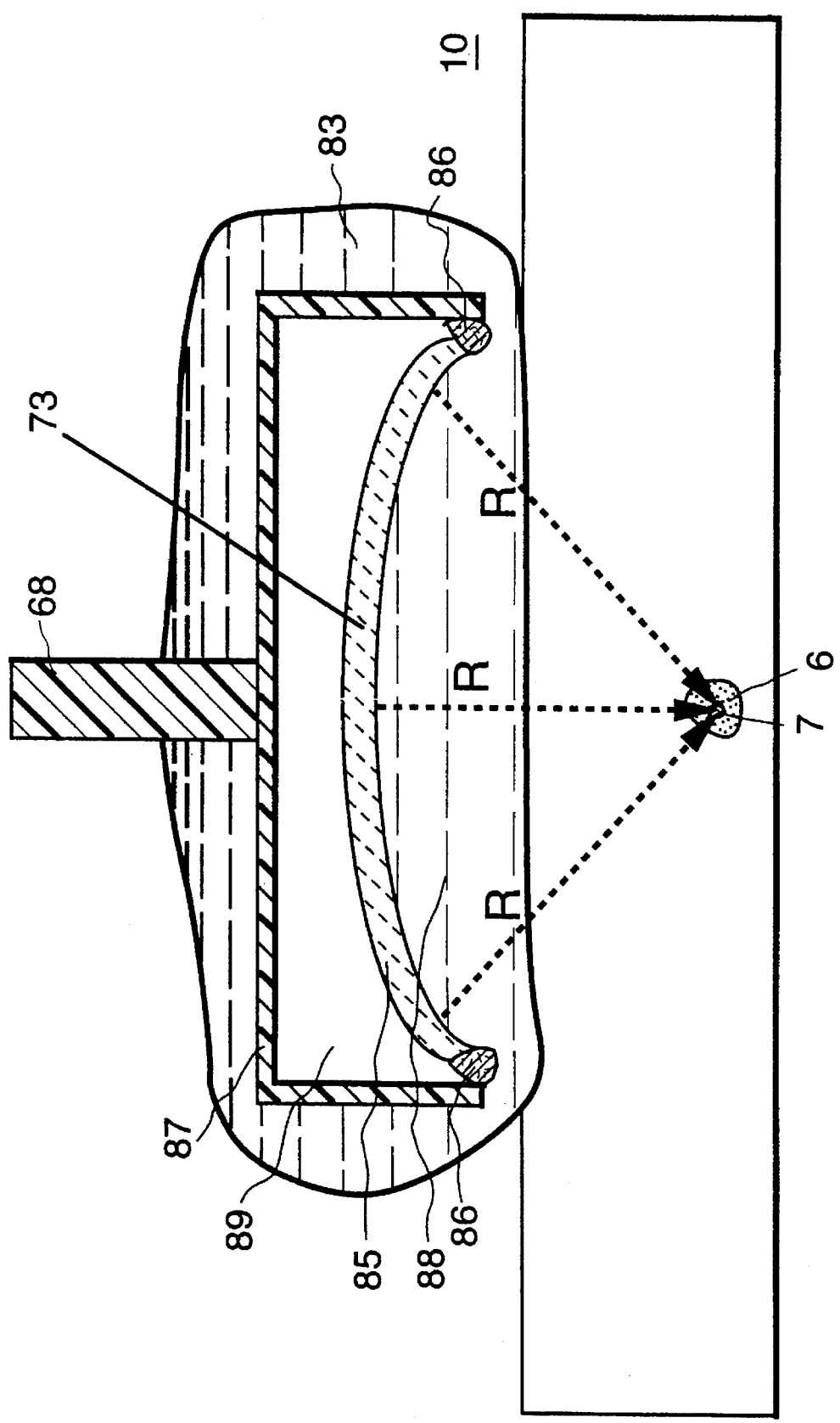
FIG. 4 is an enlarged view of the transducer of FIG. 1.

FIG. 4 shows an enlarged view of energy transducer 73 and patient interface 83. Energy transducer 73 employs a piezoelectric material 74 having a concave surface. The radius of curvature is R. When activated by a signal passed through leads 72a, 72b, piezoelectric material 74 creates pressure waves which pass through energy conducting material 88 in patient interface 83, and into patient 10 to create a heated region 7 at its focal point. When the energy transducer 73 is correctly positioned, the focal point falls within the tissue desired to be destroyed, shown here as tumor 6.

A casing 87 and a flexible seal 86 hold piezoelectric material 74 and creates an air gap 89 between casing 87 and piezoelectric material 74. Seal 86 may be conventional water-tight materials such as silicone. The purpose of air gap 89 is to minimize pressure waves being formed on the side opposite the focal point.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. An automatically positioned focussed energy system allowing a physician to selectively heat a region of a patient, comprising:

a) an open magnet magnetic resonance (MR) imaging means for providing images of internal structures of said patient;

b) an energy transducer means for focusing energy at a focal point;

c) tracking means for determining the position and orientation of the focal point of the energy transducer means;

d) display means for displaying an image;

e) general purpose computer means coupled to the tracking means, the MR imaging means, and the display means, for creating a computer generated model from the images provided by the MR imaging means having internal structures which simulate internal structures of said patient, for creating an image of the model, for receiving the location and orientation of the energy transducer means and its focal point from the tracking means, for directing the MR imaging system to acquire an actual image of internal structures of the patient at an oblique plane near the energy transducer means, and for mixing the image of the model with the actual image acquired at the oblique plane to produce a composite image and for providing the composite image to the display means for display;

f) a superposition device coupled to the tracking means and display means which functions to receive the position and orientation of the energy transducer means and superimpose a symbol indicating the position and orientation of the focal point of the energy transducer means on the composite image of the display means;

g) a pointing device coupled to the general purpose computer means, for interacting with said physician to select an internal structure of the model to be destroyed; and h) actuating means coupled to the general purpose computer means for receiving locations corresponding to the selected internal structure and scanning the focal point of the energy transducer means through these locations.

2. The automatically positioned focussed energy system of claim 1 further comprising an interactive input means for interacting with said physician to acquire a desired focal point energy intensity, and adjust the intensity of energy provided to the focal point as the point scans through locations within said internal structure.

3. The automatically positioned focussed energy system of claim 1 further comprising an interactive input means for interacting with said physician to initiate a temperature sensitive MR image to be acquired.

4. The automatically positioned focussed energy system of claim 1 further comprising an interactive input means for interacting with said physician to initiate the MR image to be acquired at the oblique plane.

5. The automatically positioned focussed energy system of claim 1 wherein the energy transducer means comprises an ultrasound transducer.

6. The automatically positioned focussed energy system of claim 1 wherein the tracking means comprises a mechanical arm attached to the energy transducer means having a plurality of joints, each joint having a position sensor for measuring its current position, the arm providing the location and orientation of the energy transducer means from the positions measured from the sensors.

7. The automatically positioned focussed energy system of claim 1 wherein the tracking means comprises a) a plurality of infrared emitters; and b) a plurality of infrared tracking units for tracking the infrared emitters and calculating a position and orientation of the energy transducer means.

* * * * *